United States Patent [19]

Fischer et al.

[11] Patent Number: 5,312,819
[45] Date of Patent: May 17, 1994

[54] PHARMACEUTICAL COMPOSITIONS COMPRISING CLOZAPINE AND A RADICAL SCAVENGER

[75] Inventors: Volker Fischer, Lörrach-Brombach, Fed. Rep. of Germany; Ronald P. Mason, Cary, N.C.

[73] Assignee: Sandoz Ltd., Basle, Switzerland

[21] Appl. No.: 739,635

[22] Filed: Aug. 2, 1991

Related U.S. Application Data

[63] Continuation-in-part of Ser. No. 717,136, Jun. 18, 1991, abandoned, which is a continuation-in-part of Ser. No. 569,689, Aug. 20, 1990, abandoned.

[51] Int. Cl.$^5$ .................. A61K 31/55; A61K 31/355; A61K 31/34; A61K 31/075
[52] U.S. Cl. .................................... 514/220; 514/458; 514/474; 514/720; 514/922
[58] Field of Search ............... 514/220, 458, 474, 720, 514/922

[56] References Cited

U.S. PATENT DOCUMENTS 4,761,411  8/1988  Glamkowski et al. ............. 514/219

OTHER PUBLICATIONS

Vanderkamp, Internat. J. of Neuropsychiatry, 2, pp. 204–206 (1966).
Merck Index, 11th Ed., #2417, Clozapine, 1989.
L. Ovesen, Drugs, vol. 27, pp. 148–170 (1984).
D. Benton, Psychopharmacology, vol. 75, pp. 98 and 99 (1981).
H. E. Lehmann, et al., Psychopharmacology Bulletin, vol. 16, No. 2, pp. 79 and 80 (1980).
T. A. Ban et al., Communications in Psychopharmacology, vol. 1, pp. 119–122 (1977).
Drug Facts and Comparisons, pp. 24–27 (1990 edition).
Rev. roum. Med. Neurol. Psychiat., vol. 14, No. 1, pp. 29–34 (1976).

Primary Examiner—Frederick E. Waddell
Assistant Examiner—Kimberly R. Jordan
Attorney, Agent, or Firm—Robert S. Honor; Melvyn M. Kassenoff; Joseph J. Borovian

[57] ABSTRACT

The invention concerns pharmaceutical compositions comprising clozapine and a radical scavenger.

7 Claims, No Drawings

PHARMACEUTICAL COMPOSITIONS COMPRISING CLOZAPINE AND A RADICAL SCAVENGER

This is a continuation-in-part of U.S. patent application Ser. No. 07/717,136, filed Jun. 18, 1991, now abandoned, which in turn is a continuation-in-part of U.S. patent application Ser. No. 07/569,689, filed Aug. 20, 1990, now abandoned.

The present invention relates to novel pharmaceutical compositions comprising clozapine and a radical scavenger preferably L-ascorbic acid.

Clozapine, having the chemical name 8-chloro-11-(4-methyl-1-piperazinyl)-5H-dibenzo[b,e][1,4]diazepine, is a neuroleptic drug.

Clinical studies have shown that clozapine is effective as an antipsychotic agent in patients who are refractory and/or intolerant to classical antipsychotic drug treatment. The compound was found to be superior in antipsychotic efficacy to standard neuroleptics; and approximately 30% of patients conservatively defined as being refractory to these neuroleptics significantly improved with clozapine treatment.

Despite its advantages, development of clozapine has been hampered by the apparent increased risk of granulocytopenia and agranulocytosis. Granulocytopenia is an established risk of treatment with tricyclic antipsychotic agents, including the phenothiazine group. Granulocytopenia is defined as a drop in the granulocyte count to less than $1500/mm^3$ in the blood; the term agranulocytosis is used when the granulocyte count drops below $500/mm^3$.

The first 18 weeks of clozapine treatment is the period of highest risk with respect to the occurrence of granulocytopenia and agranulocytosis. If onset of such a disorder goes unrecognized and treatment with the drug is not discontinued, granulocytopenia will run a progressive course of increasing severity. Complete recovery usually occurs, when the offending drug has been withdrawn.

In accordance with the present invention it has now surprisingly been found that co-administration of clozapine and a radical scavenger e.g. L-ascorbic acid, may exhibit particularly advantageous and unforeseen properties. Thus such a co-administration provides excellent antipsychotic efficacy with significantly or substantially reduced or without induction of granulocytopenia or agranulocytosis as indicated by lack of formation of reactive metabolites such as free radicals and lack of covalent binding to nucleophiles such as glutathione and protein from purified human myeloperoxidase and human leucocytes e.g. as shown in the following tests:

1) Clozapine metabolism by peroxidases was demonstrated through monitoring the disappearance of the UV absorption at 290 nm, when clozapine (100 μM) was incubated with 1-5 μg/ml of horseradish peroxidase (type VI, Sigma, USA) and 50 μM hydrogen peroxide in 0.05M phosphate buffer at pH 7.4. Metabolism of clozapine was reversed when physiological concentrations of sodium ascorbate (0.7 mM) were added to the incubation as indicated by the absence of UV signal changes.

2) Gradient reversed phase HPLC analysis combined with on-line radioactivity detection of incubations containing tritium-labeled clozapine (100 μM; labeled at positions 2,3,4 and 6), human myeloperoxidase (20 units/ml; Sigma, USA) or horseradish peroxidase (5 μg/ml, type VI; Sigma, USA) and hydrogen peroxide (400 μM) in phosphate buffer (0.05M, pH 4-7.4), revealed the formation of at least 5 metabolite peaks with retention times of 3.3, 14.7, 18.7, 20.6 and 76 minutes. For HPLC a reversed phase column (Supelco Inc., Bellefonte Pa. USA LC-18-DB, 5 μm, 250×4.6 mm) was used. The mobile phase consisted of $(NH_4)_2CO_3$ buffer pH 8.5 (solvent A) and acetonitrile (solvent B). The proportion of solvent B was 0% for 5 minutes and was increased to reach 20% at 10 minutes, 24% at 60 minutes and 80% at 100 minutes. Covalent binding of clozapine-derived material to the enzyme was indicated by the coelution of radioactivity with the enzymatic protein from the HPLC column. Metabolism of clozapine and covalent binding was dependent on the presence of the enzyme and hydrogen peroxide. Metabolism was completely reversed with physiological concentrations of sodium ascorbate (0.7 mM) i.e. no metabolites were found and no radioactivity coeluted with the enzymatic protein under such conditions. When glutathione (GSH, 10 mM, pH 7.4) was added to the standard incubation, covalent binding to the enzymatic protein and metabolite formation was also reduced but to a lesser extent. Instead two radioactive peaks eluting at 28 and 53 minutes from the HPLC appeared. These peaks were identified as clozapine glutathione conjugates at position 6 and 9 using MS- and NMR-spectroscopy after isolation by HPLC.

3) The nature of the reactive intermediates leading to covalent binding was investigated by monitoring oxygen consumption using a Clarke oxygen electrode in incubations of clozapine (100 μM), horseradish peroxidase (5 μg/ml) and GSH (10 mM) in phosphate buffer (0.05M, pH 7.4). Oxygen consumption has also been observed when horseradish peroxidase was replaced with human myeloperoxidase (10 units) and GSH with NADPH (10 mM). Oxygen consumption in this incubation indicates an initial clozapine radical formation. The clozapine radical is capable of oxidizing GSH to a thiyl radical ("thiyl pumping"), which ultimately leads to the observed oxygen consumption forming superoxide. Oxygen consumption i.e. initial clozapine radical formation was prevented in the presence of sodium ascorbate at physiological concentrations (0.7 mM).

Free radical formation in the absence of sodium ascorbate was further confirmed by electron spin resonance spectroscopy (ESR). Glutathionyl thiyl radicals were detected by radical trapping with 5,5-dimethyl-1-pyrroline-N-oxide (DMPO, 100 mM), as indicated by the four line ESR signal corresponding to the DMPO-glutathionyl thiyl radical adduct.

Additional evidence for the reduction of a clozapine radical by ascorbate arises from the over two fold increase in the steady-state concentration of the ascorbyl radical in a peroxidase system when clozapine is present. In phosphate buffer (pH 7.4, 50 mM) containing 100 μM sodium ascorbate, 100 μM clozapine, horseradish peroxidase (8.3 μg/ml) and hydrogen peroxide (50 μM), the ascorbyl radical was detected by ESR spectroscopy. The ascorbyl radical concentration was only marginally affected in the presence of 1 mM glutathione, but it was almost absent in the presence of 1 mM NADPH. In the absence of clozapine much lower concentrations of the ascorbyl radical were detected. No ESR signal was observed in the absence of hydrogen peroxide and sodium ascorbate.

4) In another test heparinized peripheral blood was obtained from normal, healthy male volunteers, and granulocytes/polymorphonuclear leucocytes (PMN's) were isolated within 1-2 hours using an isolation kit (United Technologies Packard, Los Alamos, USA). PMN's were suspended in RPMI 1640 (Gibco, Basel, Switzerland) medium and adjusted to about $4 \times 10^6$ cells/ml before fetal calf serum was added (10% v/v). After incubation of radiolabeled clozapine (100 μM, 37° C., 72 h) with the above PMN's binding of clozapine to PMN's is detected as evidenced by exhaustive extraction with methanol. A reduction of covalent binding of clozapine to PMN's may also be shown, when radiolabeled clozapine and sodium ascorbate are incubated together with PMN's.

Covalent binding to PMN's (detected by exhaustive extraction with methanol and acetonitrile) was also observed when 50 μM clozapine were incubated at 37° C. for 30 minutes in Hanks balanced salt solution with $2.5 \times 10^6$ PMN's. Binding was significantly increased when opsonized zymosan (zymosan was opsonized by incubation of 5 mg in 1 ml of fresh human serum for 30 min at 37° C. followed by washing three times in saline) was present. Addition of 5 mM sodium ascorbate to incubations containing opsonized zymosan under conditions as described above let to a reduction of clozapine binding to PMN's.

Clozapine metabolites such as 8-chloro-11-(1-piperazinyl)-5H-dibenzo[b,e][1,4]diazepine, 8-chloro-11-(4-methyl-4-oxo-1-piperazinyl)-5H-dibenzo[b,e][1,4-]diazepine, 8-hydroxy-11-(4-methyl-1-piperazinyl)-5H-dibenzo[b,e][1,4]diazepine, 8-hydroxy-11-(1-piperazinyl)-5H-dibenzo[b,e][1,4]diazepine, 8-methylthio-11-(4-methyl-1-piperazinyl)-5H-dibenzo[b,e][1,4-]diazepine and 7-hydroxy-8-chloro-11-(4-methyl-1-piperazinyl)-5H-dibenzo[b,e][1,4]diazepine, can also be shown to form reactive species such as free radicals using the tests mentioned above for clozapine. Their reactive metabolites also bind covalently to nucleophiles such as glutathione and protein from human myeloperoxidase and human leucocytes. It can also be shown that the reactive metabolites of these compounds can also be reduced by radical scavengers and covalent binding can be prevented by radical scavengers such as ascorbic acid.

These findings demonstrate that clozapine and its metabolites bind covalently also to intact human cells and that this binding can be prevented with antioxidants, such as ascorbic acid.

If desired the ascorbic acid may be replaced by an equivalent amount of another radical scavenger.

The utility of clozapine combined with a radical scavenger in the treatment of schizophrenia, is also indicated in clinical trials, e.g. effected with the doses indicated below, e.g. from 12.5 to 300 mg clozapine and from 300 to 400 mg ascorbic acid 3 times a day. These may be carried out to show the effect in the treatment of schizophrenia with significantly or substantially reduced or without induction of granulocytopenia and agranulocytosis in schizophrenic patients, in particular in schizophrenic patients who are either resistant to classical antipsychotics or who cannot tolerate them because of severe side effects.

An alternative clinical trial is as follows: In a prospective open multicenter trial 1500 patients who have never received clozapine with a diagnosis of treatment-resistant schizophrenia are studied for 26 weeks. White blood cell count (WBC) monitoring is carried out weekly. Treatment is initiated on day 1 and 2, with 25 mg clozapine + 400 mg ascorbic acid/day. Generally, this dosage is increased the following way: 50 mg clozapine + 800 mg ascorbic acid/day on days 3-4, 75 mg clozapine + 1200 mg ascorbic acid/day on days 5-6, 100 mg clozapine + 1600 mg ascorbic acid/day on days 7-8, 150 mg clozapine + 1200 mg ascorbic acid/day on days 9-10, 200 mg clozapine + 2000 mg ascorbic acid/day on days 11-12, 250 mg clozapine + 1600 mg ascorbic acid/day on days 13-14, and 300 mg clozapine + 1200 mg ascorbic acid/day on days 15-16. Maintenance dose is 200-600 mg clozapine + 1200-2400 mg ascorbic acid administered daily in divided doses on the basis of clinical judgement.

After 26 weeks only 40% or less e.g. ca 50 or 60% or less of trial subjects anticipated to develop granulocytopenia or agranulocytosis on the basis of historical controls exhibit relevant symptoms.

The co-administration of clozapine and a radical scavenger is accordingly indicated for the treatment of schizophrenia with significantly or substantially reduced or without induction of granulocytopenia or agranulocytosis.

Accordingly in yet a further aspect the present invention provides a method of treating schizophrenia with significantly or substantially reduced or without induction òr granulocytopenia or agranulocytosis in schizophrenic patients, in particular treating schizophrenic patients who are either resistant to classical antipsychotics or who cannot tolerate them because of severe side effects, in a subject in need of such treatment which method comprises concomitantly administering to said subject a therapeutically effective amount of clozapine and a radical scavenger.

The exact daily dosage of clozapine and a radical scavenger for use in the method of the invention will depend upon, inter alia, the radical scavenger employed, the mode of administration and the condition to be treated.

Suitable indicated daily dosages of clozapine for larger mammals, e.g. humans are in the range of 12.5 to 1200 mg, preferably 25 to 900 mg, more preferably 25 to 600 mg.

Radical scavengers include anti-oxidants e.g. those used in foods.

The anti-oxidants may be reducing agents such us i) L-ascorbic acid, L-ascorbic acid salts, iso-ascorbic acid and derivatives t-hereof, e.g. L-ascorbic acid 6-palmitate or phosphatidyl-L-ascorbic acid. The anti-oxidants may be e.g. ii) ($C_{1-12}$)alkyl gallates, such as propyl, octyl or dodecyl gallate, butylated hydroxy anisole, butylated hydroxy toluene, $\alpha$-, $\beta$-, $\gamma$- or $\delta$-tocopherol, $\alpha$-, $\beta$-, $\gamma$- or $\delta$-tocotrienol, 3,4-dihydro-2,5,7,8-tetramethyl-2-carboxy-2H-1-benzopyran-6-ol, 4,4'-[(1-methylethylidine)-bis(thio)-bis[2,6-bis(1,1-dimethylethyl)phenol], nordihydroguaiaretic acid, ubiquinol-10, retinol and uric acid. Other anti-oxidants include iii) ($C_{1-12}$)alkyl hydroxybenzoates, e.g. methyl, ethyl, propyl or butyl or salts thereof, e.g. sodium salt, or lazaroids.

Preferred anti-oxidants are L-ascorbic acid, L-ascorbic acid 6-palmitate, ubiquinol-10 and $\alpha$-tocopherol, especially L-ascorbic acid.

The radical scavengers are used in their effective amounts e.g. as known from literature e.g. from 1 mg to 2 g.

As a radical scavenger preferably ascorbic acid is used. If desired a salt thereof may be used, e.g. a sodium salt.

Suitable indicated daily dosages of L-ascorbic acid are in the range of from about 0.5 g to about 20 g, preferably 1 to 10 g, in particular 1 to 3 g or e.g. 3 to 8 g.

An indicated weight ratio of clozapine to L-ascorbic acid is from about 1:3 to about 1:40, or e.g. 1:10 to 1:40.

Examples of preferred amounts of clozapine in unit dosage forms are 12.5, 25, 50 and 100 mg. Examples of preferred amounts of L-ascorbic acid in unit dosage forms are 500 and 1000 mg and especially 300 mg or 400 mg. Conveniently clozapine and a radical scavenger are administered 1 to 3 times a day.

The compositions of the invention include any appropriate form suitable for enternal administration, preferably oral administration. Preferred compositions in accordance with the invention are forms suitable for oral administration such as tablets, especially effervescent tablets, sachets or capsules.

Preferably the compositions of the invention constitute an unit dosage form, whereby each unit dosage will comprise a predetermined amount of clozapine and a radical scavenger. The compositions of the invention may contain clozapine and a radical scavenger in admixture with suitable pharmaceutical diluents, carriers or other excipients suitably selected with respect to conventional pharmaceutical practice. For example, tablets, may contain beside the active agents fillers, granulating agents, disintegrating agents, binding agents, lubricating agents, stabilizing agents, dyestuffs, sweetening and flavoring agents.

Accordingly, in a further aspect the present invention provides a process for the manufacture of a pharmaceutical composition, which comprises formulating clozapine with a radical scavenger in particular intimately admixing clozapine and a radical scavenger together with a pharmaceutically acceptable diluent or carrier therefor, and optionally forming a unit dosage form.

In yet a further aspect the present invention provides a pack or dispenser-device adapted for the concomitant presentation or administration of clozapine and a radical scavenger wherein clozapine and a radical scavenger are separately arranged. Conveniently clozapine and a radical scavenger are contained in the pack or dispenser-device in separated unit dosage forms. Preferably the pack or dispenser-device bears directions for the concomitant administration of a pre-determined amount of clozapine and a radical scavenger. The directions may for example be printed directly on the pack or device.

It should be understood that the term "clozapine", when discussed hereinabove, is intended to embrace said compound in free base form, and its pharmaceutically acceptable acid addition salts.

The following Examples are illustrative of the preparations of the present invention and their manufacture.

EXAMPLE 1

Tablet

Tablets containing the ingredients below may be prepared by conventional techniques and are useful for oral administration in a dosage of e.g. 1 to 2 tablets 1 to 3 times a day in the treatment of schizophrenia.

| Ingredients | Weight (mg) |
|---|---|
| Clozapine | 50.0 |
| Ascorbic Acid | 500.0 |
| Cellulose, microcryst. | 125.0 |
| Pregelatinized Starch | 35.0 |
| Crospovidone | 17.5 |

| Ingredients | Weight (mg) |
|---|---|
| Magnesium Stearate | 2.5 |
|  | 730.0 |

The ingredients are thoroughly mixed in conventional manner and pressed into individual tablets. If desired the tablet may be shaped so that it may be easily divided into two.

EXAMPLE 2

Effervescent Tablet

Effervescent tablets containing the ingredients below may be prepared by conventional techniques and are administered at a dose of one tablet 1 to 3 times a day in the treatment of schizophrenia.

| Ingredients | Weight (mg) | | | |
|---|---|---|---|---|
|  | A | B | C | D |
| Clozapine | 100.0 | 100.0 | 100 | 25 |
| Ascorbic Acid | 1000.0 | 1000.0 | 400 | 400 |
| Sodium Ascorbate | 250.0 | 250.0 | — | — |
| Sodium Bicarbonate | 580.0 | 580.0 | 300 | 300 |
| Colloidal Siliciumdioxide | 20.0 | — | — | — |
| Stearic Acid | 50.0 | — | — | — |
| Polyethyleneglycol 6000 | — | 70.0 | 50.0 | 50 |
|  | 2000.0 | 2000.0 | 850.0 | 775.0 |

EXAMPLE 3

Granules filled into sachets

Granules containing the ingredients indicated below may be prepared by conventional techniques and are administered at a dose of 1–2 sachet 1 to 3 times a day in the treatment of schizophrenia.

| Ingredients | Sachet Weight (mg) | |
|---|---|---|
|  | A | B |
| Clozapine | 100.0 | 100.0 |
| Ascorbic Acid | 1250.0 | 1250.0 |
| Sodium Ascorbate | 150.0 | 150.0 |
| Lactose | 100.0 | 100.0 |
| Mannitol | 300.0 | 300.0 |
| Sodium Laurylsulfate | 5.0 | — |
|  | 1905.0 | 1900.0 |

EXAMPLE 4

Hard gelatine capsules

Hard gelatine capsules containing the ingredients below may be prepared by conventional techniques and are useful for oral administration in a dosage of e.g. 1 to 2 capsules a) or b) 1 to 3 times a day in the treatment of schizophrenia.

| Ingredients | Weight (mg) | |
|---|---|---|
|  | a) | b) |
| Clozapine | 25 | 100 |
| Ascorbic Acid | 300 | 300 |
| Lactose | 46 | 71 |
| Corn starch | 25 | 25 |
| Siliciumdioxide | 2 | 2 |
| Magnesium Stearate | 2 | 2 |
|  | 400 | 500 |

We claim:

1. A method of inhibiting the formation of granulocytopenia and agranulocytosis upon enteral administration of clozapine-containing compositions to schizophrenic patients comprising concomitantly administering to said patients a granulocytopenia- and agranulocytosis-inhibiting amount of a radical scavenger.

2. A method according to claim 1 wherein the radical scavenger is selected from the group consisting of L-ascorbic acid, L-ascorbic acid 6-palmitate, ubiquinol-10 and α-tocopherol.

3. A method according to claim 2 wherein the radical scavenger is L-ascorbic acid.

4. A method according to claim 3 wherein the L-ascorbic acid is administered at a daily dosage of between 0.5 and 20 g.

5. A method according to claim 4 wherein the L-ascorbic acid is administered at a daily dosage of between 1 and 10 g.

6. A method according to claim 3 wherein the weight ratio of clozapine to L-ascorbic acid is from about 1:3 to about 1:40.

7. A method according to claim 6 wherein the weight ratio of clozapine to L-ascorbic acid is from 1:10 to 1:40.

* * * * *